US011534445B2

(12) United States Patent
Lee

(10) Patent No.: US 11,534,445 B2
(45) Date of Patent: Dec. 27, 2022

(54) COMPOSITIONS AND METHODS FOR IMMUNE-MEDIATED CANCER THERAPY

(71) Applicant: Teclison Limited, Grand Cayman (KY)

(72) Inventor: Ruey-min Lee, Short Hills, NJ (US)

(73) Assignee: Teclison Limited, Grand Cayman (KY)

( * ) Notice: Subject to any disclaimer, the term of this patent is extended or adjusted under 35 U.S.C. 154(b) by 0 days.

(21) Appl. No.: 15/956,702

(22) Filed: Apr. 18, 2018

(65) Prior Publication Data

US 2019/0070186 A1  Mar. 7, 2019

Related U.S. Application Data

(63) Continuation of application No. PCT/US2016/058303, filed on Oct. 21, 2016.

(60) Provisional application No. 62/244,457, filed on Oct. 21, 2015.

(51) Int. Cl.

| | | |
|---|---|---|
| *A61K 31/53* | (2006.01) | |
| *A61K 35/17* | (2015.01) | |
| *A61K 39/395* | (2006.01) | |
| *C07K 16/28* | (2006.01) | |
| *A61K 31/09* | (2006.01) | |
| *A61K 31/485* | (2006.01) | |
| *A61P 35/00* | (2006.01) | |
| *A61K 31/05* | (2006.01) | |
| *A61K 31/136* | (2006.01) | |
| *A61K 31/27* | (2006.01) | |
| *A61K 31/352* | (2006.01) | |
| *A61K 39/00* | (2006.01) | |

(52) U.S. Cl.
CPC ............. *A61K 31/53* (2013.01); *A61K 31/05* (2013.01); *A61K 31/09* (2013.01); *A61K 31/136* (2013.01); *A61K 31/27* (2013.01); *A61K 31/352* (2013.01); *A61K 31/485* (2013.01); *A61K 35/17* (2013.01); *A61K 39/395* (2013.01); *A61K 39/39541* (2013.01); *A61P 35/00* (2018.01); *C07K 16/2818* (2013.01); *A61K 2039/505* (2013.01); *C07K 2317/73* (2013.01)

(58) Field of Classification Search
CPC ..................................................... A61K 31/53
See application file for complete search history.

(56) References Cited

U.S. PATENT DOCUMENTS

| 4,932,412 | A | 6/1990 | Goldenberg | |
|---|---|---|---|---|
| 9,649,316 | B2 | 5/2017 | Lee et al. | |
| 9,724,395 | B2 * | 8/2017 | King | ............. A61K 38/2046 |
| 2009/0311304 | A1 | 12/2009 | Borck et al. | |
| 2012/0087913 | A1 * | 4/2012 | Lee | .................... A61K 31/167 424/133.1 |
| 2015/0202291 | A1 | 7/2015 | Bosch et al. | |

FOREIGN PATENT DOCUMENTS

| CN | 102026634 | A | 4/2011 |
|---|---|---|---|
| JP | 2011516565 | A | 5/2011 |
| WO | WO-0124684 | A2 | 4/2001 |
| WO | WO-2009126705 | A2 | 10/2009 |
| WO | WO-2015035112 | A1 | 3/2015 |
| WO | WO-2015069770 | A1 | 5/2015 |
| WO | WO-2015089114 | A1 | 6/2015 |
| WO | WO-2017004532 | A1 | 1/2017 |
| WO | WO-2017070606 | A1 | 4/2017 |

OTHER PUBLICATIONS

Tsochatzis et al. "Transarterial Chemoembolization, Transarterial Chemotherapy, and Intra-arterial Chemotherapy for Heptocellular Carcinoma Treatment", Seminars in Oncology, 2010, vol. 37, issue 2, pp. 89-93 (Year: 2010).*
International Search Report and Written Opinion dated Dec. 29, 2016 for International PCT Patent Application No. PCT/US2016/058303.
Lencioni, et al., Lipiodol Transarterial Chemoembolization for Hepatocellular Carcinoma: A Systematic Review of Efficacy and Safety Data, Hepatology, 1-77, 2016.
Lencioni, et al., Sorafenib or placebo plus TACE with doxorubicin-eluting beads for intermediate stage HCC: The SPACE trial, Journal of Hepatology 2016, 9 pages.
EP16858387.0 Extended European Search Report dated Jun. 25, 2019.
Sonoda, et al. Enhanced antitumor effect of tirapazamine delivered intraperitoneally to VX2 liver tumor-bearing rabbits subjected to transarterial hepatic embolization. Cardiovasc Intervent Radiol. Dec. 2011; 34(6):1272-1277. doi: 10.1007/s00270-011-0156-4. Epub Apr. 9, 2011.
Disilvestro, et al. Phase III randomized trial of weekly cisplatin and irradiation versus cisplatin and tirapazamine and irradiation in stages IB2, IIA, IIB, IIIB, and IVA cervical carcinoma limited to the pelvis: a Gynecologic Oncology Group study. J Clin Oncol. Feb. 10, 2014. 32(5):458-64. doi: 10.1200/JCO.2013.51.4265. Epub Jan. 6, 2014.
Grothey, et al. Regorafenib monotherapy for previously treated metastatic colorectal cancer (CORRECT): an international, multicentre, randomised, placebo-controlled, phase 3 trial. Lancet. Jan. 26, 2013;381(9863):303-12. doi: 10.1016/S0140-6736(12)61900-X. Epub Nov. 22, 2012.

(Continued)

*Primary Examiner* — Yong S. Chong
(74) *Attorney, Agent, or Firm* — Wilson Sonsini Goodrich & Rosati

(57) ABSTRACT

Disclosed herein are methods and compositions for enhancing an immune response to a solid tumor in a subject. In some embodiments, a method comprises: (a) administering to the subject a hypoxia-activated bioreductive agent (HABA); (b) inducing hypoxia by (i) administering a hypoxia-inducing agent to the subject or (ii) embolizing one or more blood vessels supplying the solid tumor; and (c) administering an immune checkpoint inhibitor prior to, simultaneously with, or subsequent to step (b) in an amount effective to enhance an immune response to the solid tumor, as compared to an immune response in the absence of the immune checkpoint inhibitor. Kits for use in the disclosed methods are also provided.

10 Claims, 8 Drawing Sheets
(6 of 8 Drawing Sheet(s) Filed in Color)

(56) References Cited

OTHER PUBLICATIONS

Koopman, et al. Deficient mismatch repair system in patients with sporadic advanced colorectal cancer. Br J Cancer. Jan. 27, 2009. 100(2):266-73. doi: 10.1038/sj.bjc.6604867.

Le, et al. PD-1 Blockade in Tumors with Mismatch-Repair Deficiency. N Engl J Med. Jun. 25, 2015;372(26):2509-20. doi: 10.1056/NEJMoa1500596. Epub May 30, 2015.

Mahipal, et al. Immunotherapy in Hepatocellular Carcinoma: Is There a Light at the End of the Tunnel?. Cancers (Basel). Jul. 30, 2019. 11(8). pii: E1078. doi: 10.3390/cancers11081078.

Mayer, et al. Randomized Trial of TAS-102 for Refractory Metastatic Colorectal Cancer. The New England Journal of Medicine. May 14, 2015. 372. 1909-19. DOI: 10.1056/NEJMoa1414325.

Oliveira, et al. Review of PD-1/PD-L1 Inhibitors in Metastatic dMMR/MSI-H Colorectal Cancer. Frontiers in Oncology. May 14, 2019. 9:396. doi: 10.3389/fonc.2019.00396. eCollection 2019.

Rischin, et al. Tirapazamine, cisplatin, and radiation versus cisplatin and radiation for advanced squamous cell carcinoma of the head and neck (TROG 02.02, HeadSTART): a phase III trial of the Trans-Tasman Radiation Oncology Group. J Clin Oncol. Jun. 20, 2010;28(18):2989-95. doi: 10.1200/JCO.2009.27.4449. Epub May 17, 2010.

Wang, et al. Efficacy and safety of anti-PD-1/PD-L1 agents vs chemotherapy in patients with gastric or gastroesophageal junction cancer: a systematic review and meta-analysis. Medicine (Baltimore). Nov. 2019. 98(47):e18054. doi: 10.1097/MD.0000000000018054.

Williamson, et al. Phase III trial of paclitaxel plus carboplatin with or without tirapazamine in advanced non-small-cell lung cancer: Southwest Oncology Group Trial S0003. J Clin Oncol. Dec. 20, 2005;23(36):9097-9104.

Bedikian, et al. Phase II trial of tirapazamine combined with cisplatin in chemotherapy of advanced malignant melanoma. Ann Oncol. Apr. 1997;8(4):363-367. doi: 10.1023/a:1008249232000.

Brown, J.M. SR 4233 (Tirapazamine): a new anticancer drug exploiting hypoxia in solid tumours. Br J Cancer. Jun. 1993;67(6):1163-1170. doi: 10.1038/bjc.1993.220.

Chakedis, et al. Surgical Treatment of Metastatic Colorectal Cancer. Surg Oncol Clin N Am. Apr. 2018;27(2):377-399. doi: 10.1016/j.soc.2017.11.010. Epub Dec. 15, 2017. (Abstract Only).

Ciombor, et al. A Comprehensive Review of Sequencing and Combination Strategies of Targeted Agents in Metastatic Colorectal Cancer. Oncologist. Jan. 2018;23(1):25-34. doi: 10.1634/theoncologist.2017-0203. Epub Oct. 11, 2017.

ClinicalTrials.gov. A Study Evaluating TAS-102 Plus Nivolumab in Patients With MSS CRC. ClinicalTrials.gov Identifier: NCT02860546. First Posted Aug. 9, 2016. 8 pages.

ClinicalTrials.gov. A Study of Biomarker-Driven Therapy in Metastatic Colorectal Cancer (mCRC) (MODUL). ClinicalTrials.gov Identifier: NCT02291289. First Posted Nov. 14, 2014. 16 pages.

ClinicalTrials.gov. Combination of TATE and PD-1 Inhibitor in Liver Cancer (TATE-PD1). ClinicalTrials.gov Identifier: NCT03259867. First Posted Aug. 24, 2017. 9 pages.

ClinicalTrials.gov. Dose-defining Study of Tirapazamine Combined With Embolization in Liver Cancer. ClinicalTrials.gov Identifier: NCT02174549. First Posted Jun. 25, 2014. 7 pages.

ClinicalTrials.gov. TATE Versus TACE in Intermediate Stage HCC (TATE). ClinicalTrials.gov Identifier: NCT03145558. First Posted May 9, 2017. 8 pages.

Corcoran, et al. Combined BRAF and MEK Inhibition With Dabrafenib and Trametinib in BRAF V600-Mutant Colorectal Cancer. J Clin Oncol. Dec. 1, 2015; 33(34): 4023-4031. Published online Sep. 21, 2015. doi: 10.1200/JCO.2015.63.2471.

Cremolini, et al. First-line chemotherapy for mCRC—a review and evidence-based algorithm. Nat Rev Clin Oncol. Oct. 2015;12(10):607-619. doi: 10.1038/nrclinonc.2015.129. Epub Jul. 28, 2015. (Abstract Only).

Crispe, I.N. Immune tolerance in liver disease. Hepatology. Dec. 2014;60(6):2109-2117. doi: 10.1002/hep.27254. Epub Sep. 26, 2014.

Gryfe, et al. Tumor microsatellite instability and clinical outcome in young patients with colorectal cancer. N Engl J Med. Jan. 13, 2000;342(2):69-77. doi: 10.1056/NEJM200001133420201.

Hamanishi, et al. PD-1/PD-L1 blockade in cancer treatment: perspectives and issues. Int J Clin Oncol. Jun. 2016;21(3):462-473. doi: 10.1007/s10147-016-0959-z. Epub Feb. 22, 2016.

Katsanos, et al. Comparative effectiveness of different transarterial embolization therapies alone or in combination with local ablative or adjuvant systemic treatments for unresectable hepatocellular carcinoma: A network meta-analysis of randomized controlled trials. PLoS One. Sep. 21, 2017;12(9):e0184597. doi: 10.1371/journal.pone.0184597. eCollection 2017.

Kim, et al. Programmed Necrosis and Disease: We interrupt your regular programming to bring you necroinflammation. Cell Death Differ. Jan. 2019;26(1):25-40. doi: 10.1038/S41418-018-0179-3. Epub Oct. 22, 2018.

Lin, et al. Hypoxia-activated cytotoxic agent tirapazamine enhances hepatic artery ligation-induced killing of liver tumor in HBx transgenic mice. Proc Natl Acad Sci U S A. Oct. 18, 2016;113(42):11937-11942.

Maluf, et al. Phase II study of tirapazamine plus cisplatin in patients with advanced or recurrent cervical cancer. Int J Gynecol Cancer. May-Jun. 2006;16(3):1165-1171. doi: 10.1111/j.1525-1438.2006.00454.x.

Massmann, et al. Transarterial chemoembolization (TACE) for colorectal liver metastases—current status and critical review. Langenbecks Arch Surg. Aug. 2015;400(6):641-659. doi: 10.1007/S00423-015-1308-9. Epub Jun. 19, 2015.

Miller, et al. Phase II study of the combination of the novel bioreductive agent, tirapazamine, with cisplatin in patients with advanced non-small-cell lung cancer. Ann Oncol. Dec. 1997;8(12):1269-71.

Prahallad, et al. Unresponsiveness of colon cancer to BRAF(V600E) inhibition through feedback activation of EGFR. Nature. Jan. 26, 2012;483(7387):100-103. doi: 10.1038/nature10868.

Senan, et al. Phase I and pharmacokinetic study of tirapazamine (SR 4233) administered every three weeks. Clin Cancer Res. Jan. 1997;3(1):31-8.

Siegel, et al. Cancer statistics, 2018. CA Cancer J Clin. Jan. 2018;68(1):7-30. doi: 10.3322/caac.21442. Epub Jan. 4, 2018.

Van Hazel, et al. SIRFLOX: Randomized Phase III Trial Comparing First-Line mFOLFOX6 (Plus or Minus Bevacizumab) Versus mFOLFOX6 (Plus or Minus Bevacizumab) Plus Selective Internal Radiation Therapy in Patients With Metastatic Colorectal Cancer. J Clin Oncol. May 20, 2016;34(15):1723-1731. doi: 10.1200/JCO.2015.66.1181. Epub Feb. 22, 2016.

Wang, et al. A Reservoir of Mature Cavity Macrophages that Can Rapidly Invade Visceral Organs to Affect Tissue Repair. Cell. Apr. 21, 2016;165(3):668-678. doi: 10.1016/j.cell.2016.03.009. Epub Apr. 7, 2016.

Abi-Jaoudeh, et al. Phase I Trial on Arterial Embolization with Hypoxia Activated Tirapazamine for Unresectable Hepatocellular Carcinoma. J Hepatocell Carcinoma. May 17, 2021;8:421-434. doi: 10.2147/JHC.S304275. eCollection 2021.

Callahan, et al. At the bedside: CTLA-4- and PD-1-blocking antibodies in cancer immunotherapy. J Leukoc Biol. Jul. 2013;94(1):41-53. doi: 10.1189/jlb.1212631. Epub May 10, 2013.

ClinicalTrials.gov. TATE and Pembrolizumab (MK3475) in mCRC and NSCLC. ClinicalTrials.gov Identifier: NCT04701476. First Posted Jan. 8, 2021. 7 pages.

Finn, et al. Atezolizumab plus Bevacizumab in Unresectable Hepatocellular Carcinoma. N Engl J Med. May 14, 2020;382(20):1894-1905. doi: 10.1056/NEJMoa1915745.

Finn, et al. Pembrolizumab As Second-Line Therapy in Patients With Advanced Hepatocellular Carcinoma in KEYNOTE-240: A Randomized, Double-Blind, Phase III Trial. J Clin Oncol. Jan. 20, 2020;38(3):193-202. doi: 10.1200/JCO.19.01307. Epub Dec. 2, 2019.

Govaert, et al. Hypoxia after liver surgery imposes an aggressive cancer stem cell phenotype on residual tumor cells. Ann Surg. Apr. 2014;259(4):750-759. doi: 10.1097/SLA.0b013e318295c160.

(56) References Cited

OTHER PUBLICATIONS

Iñarrairaegui, et al. Immunotherapy of Hepatocellular Carcinoma: Facts and Hopes. Clin Cancer Res. Apr. 1, 2018;24(7):1518-1524. doi: 10.1158/1078-0432.CCR-17-0289. Epub Nov. 14, 2017.

Melero, et al. Evolving synergistic combinations of targeted immunotherapies to combat cancer. Nat Rev Cancer. Aug. 2015;15(8):457-472. doi: 10.1038/nrc3973.

Yu, et al. Liver metastasis restrains immunotherapy efficacy via macrophage-mediated T cell elimination. Nat Med. Jan. 2021;27(1):152-164. doi: 10.1038/s51591-020-1131-x. Epub Jan. 4, 2021.

Zheng, et al. Liver cancer incidence and mortality in China: Temporal trends and projections to 2030. Chin J Cancer Res. Dec. 2018;30(6):571-579. doi: 10.21147/j.issn.1000-9604.2018.06.01.

* cited by examiner

| Group | N | Treatment | Dose (mg/kg) | Dosing Route | Schedule |
|---|---|---|---|---|---|
| 1 | 6 | Vehicle Control | 0 | i.p. | Q2d, Day 4 – Day 14 |
| 2 | 6 | Anti-m-PD 1 | 10 mg/kg | i.p. | Q2d, Day 4 – Day 14 |
| 3 | 6 | TPZ | 30 mg/kg | i.p. | Day 0 and Day 2 |
| 4 | 6 | DMXAA | 10 mg/kg | i.p. | Day 0 and Day 2 |
| 5 | 6 | Combretastatin A-4 P | 10 mg/kg | i.v. | Day 0 and Day 2 |
| 6 | 6 | TPZ<br>Combretastatin A-4 P | 30 mg/kg<br>10 mg/kg | i.p.<br>i.v. | Day 0 and Day 2<br>Day 0 and Day 2, 2 min after TPZ injection |
| 7 | 6 | TPZ<br>DMXAA | 30 mg/kg<br>10 mg/kg | i.p.<br>i.p. | Day 0 and Day 2<br>Day 0 and Day 2, 2 min after TPZ injection |
| 8 | 6 | TPZ<br>Combretastatin A-4 P<br>Anti-m-PD 1 | 30 mg/kg<br>10 mg/kg<br>10 mg/kg | i.p.<br>i.v.<br>i.p. | Day 0 and Day 2<br>Day 0 and Day 2, 2 min after TPZ injection<br>Q2d, Day 4 – Day 14 |
| 9 | 6 | TPZ<br>DMXAA<br>Anti-m-PD 1 | 30 mg/kg<br>10 mg/kg<br>10 mg/kg | i.p.<br>i.p.<br>i.p. | Day 0 and Day 2<br>Day 0 and Day 2, 2 min after TPZ injection<br>Q2d, Day 4 – Day 14 |

FIG. 6

| | |
|---|---|
| Vehicle | 24.22±2.59 |
| TPZ | 27.32±9.56 |
| PD-1 | 24.68±11.72 |
| DMXAA | 31.01±8.17 |
| ComA4P | 13.73±5.79 |
| TPZ+ComA4P | 23.28±8.15 |
| TPZ+DMXAA | 33.14±6.59 |
| TPZ+ComA4P+PD-1 | 41.36±6.96* |
| TPZ+DMXAA+PD-1 | 29.61±9.29 |

FIG. 8

COMPOSITIONS AND METHODS FOR IMMUNE-MEDIATED CANCER THERAPY

CROSS-REFERENCE

This application is a continuation application of International Patent Application No. PCT/US2016/058303, filed on Oct. 21, 2016, which application claims priority to U.S. Provisional Patent Application No. 62/244,457, filed on Oct. 21, 2015, each of which is herein incorporated by reference in its entirety for all purposes.

BACKGROUND OF THE INVENTION

Although some patients have been shown to exhibit immunity toward cancer based on the detection of tumor-specific cytotoxic T cells, these T cells appeared to be shielded from the tumor without conferring much if any therapeutic or protective benefit. Some explain the discrepancy with the theory that tumors evolve various mechanisms to avoid immune attack. For a normal immune reaction to occur, APCs uptake tumor-derived antigens and present them to T cells after processing to prime the T cells to develop cytotoxicity against the tumor cells that carry the antigen. The interaction between APCs and T cells is regulated by various ligand-receptor interactions, including the T cell receptor (TCR) that recognizes tumor-associated antigen and forms a complex with MHC molecules, and co-activator CD28. CTLA4 functions as a negative regulator of T cells, and CD40 functions as a positive regulator for APCs. PD-1 is another negative regulator of cytotoxic T cells, and serves as an immune checkpoint. Tumor cells can express a PD-1 ligand, called PD-L1, which activates PD-1 and thus suppresses anti-tumor activity of the T cells. Tumors may also recruit regulatory T cells, which can suppress cytotoxic T cell activity to protect tumor from immune attack. Efforts have been made to manipulate immune signaling responses for treating cancer, but response rates and effects on progress-free survival leave much room for improvement. Moreover, relying too heavily on compounds that dampen immune suppression could tip the balance of the immune system toward autoimmune disorders. For example, the observed adverse effects of nivolumab and pembrolizumab include various immune-related hepatitis, pneumonitis, hypophysitis, colitis and others, indicating that further enhancement of general immunity may carry potential risks.

SUMMARY OF THE INVENTION

In view of the foregoing, there is a need for improved compositions and strategies for the treatment of cancer, particularly those that employ an immune response in the subject. The present disclosure addresses this need, and provides other advantages as well. In some of the embodiments disclosed herein, methods are provided for enhancing an immune response against a solid tumor by combining an induction of necrosis in the tumor (increasing immune system exposure to tumor antigens) with administration of an immune checkpoint inhibitor.

In one aspect, the present disclosure provides a method of enhancing an immune response to a solid tumor in a subject, the method comprising: (a) administering to the subject a hypoxia-activated bioreductive agent (HABA); (b) inducing hypoxia by (i) administering a hypoxia-inducing agent to the subject or (ii) embolizing one or more blood vessels supplying the solid tumor; and (c) administering an immune checkpoint inhibitor prior to, simultaneously with, or subsequent to step (b) in an amount effective to enhance an immune response to the solid tumor, as compared to an immune response in the absence of the immune checkpoint inhibitor. In some embodiments, the hypoxia-activated bioreductive agent is tirapazamine. In some embodiments, step (b) comprises administering a hypoxia-inducing agent that is a vascular disrupting agent. In some embodiments, the vascular disrupting agent is DMXAA, a stilbene, or a stilbene derivative. In some embodiments, the stilbene derivative is selected from the group consisting of: combretastatin, combretastatin derivatives, cis-3,4',5-trimethoxy-3'-aminostilbene (stilbene 5c), cis-3,4',5-trimethoxy-3'-hydroxystilbene (stilbene 6c), and a prodrug morpholino-carbamate derivative of stilbene 5c. In some embodiments, step (b) comprises administering a hypoxia-inducing agent that is an anti-angiogenic agent. In some embodiments, the hypoxia-activated agent and the hypoxia-inducing agent are administered in amounts effective to induce necrosis of at least 75% of the solid tumor. In some embodiments, step (b) comprises embolizing the one or more blood vessels by administering an embolizing agent. In some embodiments, the immune checkpoint inhibitor is an inhibitor of PD-1, PD-L1, or CTLA-4. In some embodiments, the immune checkpoint inhibitor is a monoclonal antibody. In some embodiments, the monoclonal antibody is selected from the group consisting of: nivolumab, pembrolizumab, atezolizumab, MEDI4736, and ipilimumab. In some embodiments, the solid tumor is a tumor selected from the group consisting of: hepatocellular carcinoma, cholangiocarcinoma, metastatic colorectal cancer in liver, lung cancer, breast cancer, colorectal cancer, bladder cancer, head and neck cancer, ovarian cancer, and pancreatic cancer. In some embodiments, step (b) comprises trans-arterial embolization. In some embodiments, step (b) is performed after step (a). In some embodiments, step (b) comprises administering a hypoxia-inducing agent. In some embodiments, step (c) comprises administering the immune checkpoint inhibitor two or more times after step (b). In some embodiments, administering the immune checkpoint regulator is effective in maintaining the solid tumor at a size that is less than 50% of a pre-treatment size for at least 6 months. In some embodiments, the combination of administering the HABA, inducing hypoxia, and administering the immune checkpoint inhibitor exhibit a synergistic effect in treating a proliferative disorder in the subject.

In one aspect, the present disclosure provides a kit for use in enhancing an immune response to a solid tumor in a subject. In some embodiments, the kit comprises: (a) a hypoxia-activated bioreductive agent (HABA); (b) a hypoxia-inducing agent or an embolizing agent; and (c) an immune checkpoint inhibitor. In some embodiments, the HABA is tirapazamine. In some embodiments, part (b) is a hypoxia-inducing agent that is a vascular disrupting agent. In some embodiments, the vascular disrupting agent is DMXAA, a stilbene, or a stilbene derivative. In some embodiments, the stilbene derivative is selected from the group consisting of: combretastatin, combretastatin derivatives, cis-3,4',5-trimethoxy-3'-aminostilbene (stilbene 5c), cis-3,4',5-trimethoxy-3'-hydroxystilbene (stilbene 6c), and a prodrug morpholino-carbamate derivative of stilbene 5c. In some embodiments, part (b) is a hypoxia-inducing agent that is an anti-angiogenic agent. In some embodiments, the immune checkpoint inhibitor is an inhibitor of PD-1, PD-L1, or CTLA-4. In some embodiments, the immune checkpoint inhibitor is a monoclonal antibody. In some embodiments, the monoclonal antibody is selected from the group consisting of: nivolumab, pembrolizumab, atezolizumab, MEDI4736, and ipilimumab.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 provides a table describing the experimental design of a study evaluating the pathology and immunohistochemistry of administering of anti-mPD-1, tirapazamine (TPZ), combretastatin A4 phosphate, 5,6-Dimethylxantheonone-4-acetic acid (DMXAA), and various combinations thereof in the treatment of a subcutaneous 3LL lung syngenic cancer model in C57BL/6 mice.

FIG. 8 is a table that provides the percentage of tumor necrosis in the H&E stained 3LL tumor tissue sections depicted in FIG. 7.

DETAILED DESCRIPTION OF THE INVENTION

Figure 1:
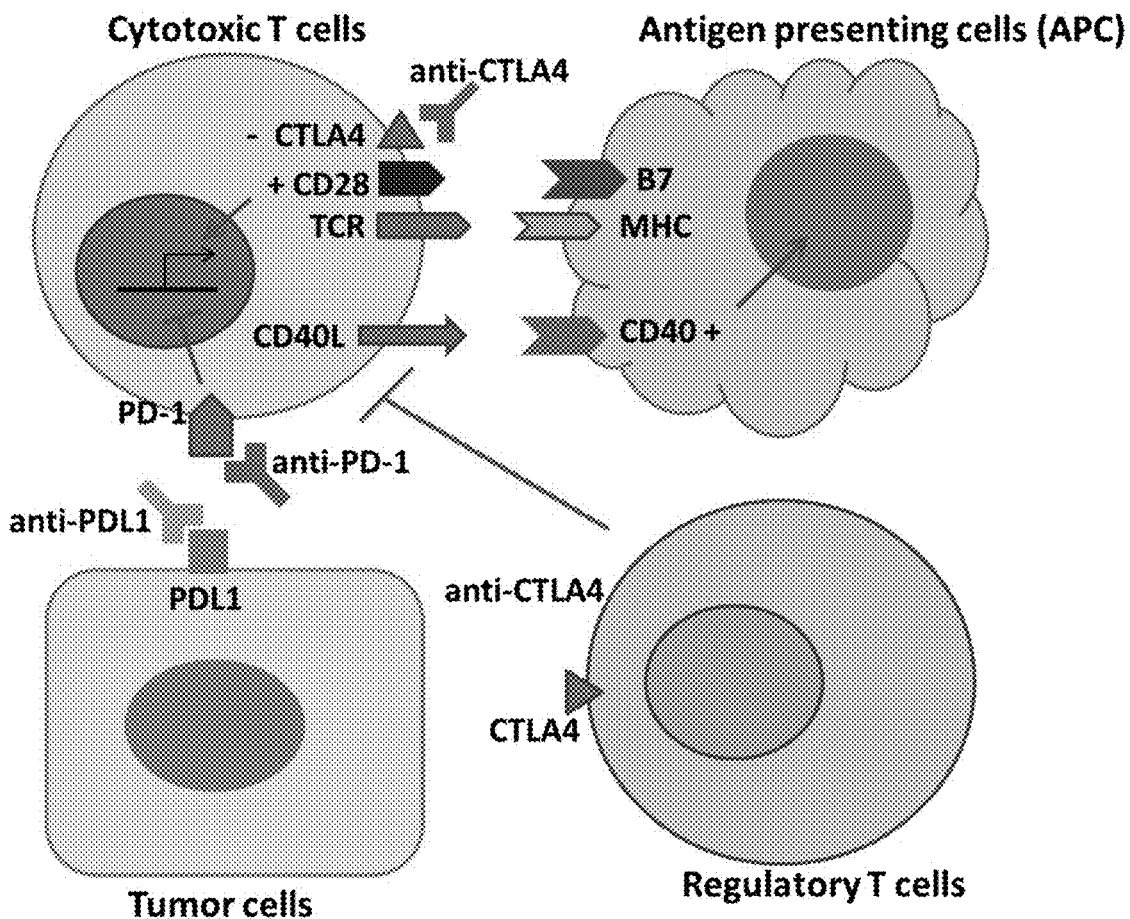
FIG. 1 provides an example diagram to illustrate interactions and regulation among tumor cells, cytotoxic T cells, antigen presenting cells (APC) and regulatory T cells. The diagram illustrates how blocking checkpoints PD-1, PD-L1, or CTLA4 can modulate immune suppressive effects within a tumor.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "therapeutic agent", "therapeutically capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. Typically, prophylactic benefit includes reducing the incidence and/or worsening of one or more diseases, conditions, or symptoms under treatment (e.g. as between treated and untreated populations, or between treated and untreated states of a subject).

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions (e.g., administration of separate compositions sequentially), or administration in a composition in which both agents are present.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein.

A "synergistic" or "synergizing" effect can be such that the one or more effects of the combination compositions are greater than the one or more effects of each component alone, or they can be greater than the sum of the one or more effects of each component alone. The synergistic effect can be about, or greater than about 10%, 20%, 30%, 50%, 75%, 100%, 110%, 120%, 150%, 200%, 250%, 350%, or 500% or even more than the effect on a subject with one of the components alone, or the additive effects of each of the components when administered individually. The effect can be any of the measurable effects described herein.

In one aspect, the present disclosure provides a method of enhancing an immune response to a solid tumor in a subject. In some embodiments, the method comprises (a) administering to the subject a hypoxia-activated bioreductive agent (HABA); inducing hypoxia after step (a) by (i) administering a hypoxia-inducing agent to the subject or (ii) embolizing one or more blood vessels supplying the solid tumor, wherein the HABA and hypoxia are effective in inducing necrosis of the solid tumor; and (c) administering an immune checkpoint inhibitor prior to, simultaneously with, or subsequent to step (b) in an amount effective to enhance an immune response to the solid tumor, as compared to an immune response in the absence of the immune checkpoint inhibitor.

In general, a hypoxia-activated bioreductive agent (HABA) is a compound which in the presence of oxygen, is an inactive prodrug, and in a low oxygen environment (e.g. hypoxia) is converted to an active form having an increased activity relative to the prodrug form. In some embodiments, an increased activity in a low oxygen environment is evidenced by a level of tumor cell death within a solid tumor that is greater when administration is carried out according to methods described herein (e.g. when local regions of hypoxia are generated in the tumor, or in an area that contains the tumor, by methods described herein), than when the same amount of a hypoxia-activated bioreductive agent is administered to a solid tumor, or an area containing a solid tumor, but regions of hypoxia are not generated by methods described herein. In some embodiments, the increase in activity is at least about 10 fold, or greater, and the increase may be much higher e.g. from about 20-200 fold, or from about 50 to 200 fold, or 100 to 200 fold, or more. Examples of HABAs include, but are not limited to tirapazamine, banoxantrone (AQ4N), porfiromycin, apaziquone (EO9), 1,2-bis(methylsulfonyl)-1-(2-chloroethyl)-2-[[1-(4-nitrophenyl)ethoxy]carbonyl]hydrazine (KS119), dinitrobenzamide mustard derivative (such as PR 104) and 4-[3-(2-nitro-1-imidazolyl)-propylamino]-7-chloroquinoline hydrochloride (NLCQ-1, NSC 709257). Additional examples include, but are not limited to nitroimidazoles misonidazole, etanidazole, and nimorazole, TG-302, SN30000, mitomycin C (MMC), porfiromycin, RH1, and EO9 (apaziquone). In some embodiments, the HABA is tirapazamine. In some embodiments, the tirapazamine has a structure

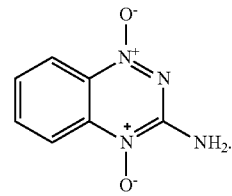 [SMILES: Nc1n[n+]([O-])c2ccccc2[n+]1[O-]]

In some embodiments, a hypoxic region is a region where the level of oxygen is less than about 10%, and preferably less than about 5%. In some embodiments, the level of oxygen in the hypoxic region is about 10, 9, 8, 7, 6, 5, 4, 3, 2, or 1%. In some embodiments, an oxygen level of about 10% or lower, and preferably about 5% or lower, is sufficient to activate hypoxia-activated bioreductive agents such as tirapazamine to a level that is at least 10-fold more active than the prodrug form. Those of skill in the art are familiar with the measurement of oxygen levels in biological systems, and are also aware that oxygen measurements may be expressed in "mm Hg", wherein, for example, 10% $O_2$ is equal to about 76 mmHg and 1% $O_2$ is equal to about 7.6 mmHg.

A HABA can be activated by inducing hypoxia, which is advantageously performed after administration of the HABA. Any of a variety of strategies may be employed for inducing a localized hypoxic region within which the bioreductive agent is activated. In some embodiments, this is accomplished by mechanical embolization of one or more blood vessels that supply the targeted region, such as by administration of embolizing agents or devices through a catheter placed by interventional radiologists to occlude the vessel mechanically. In some embodiments, hypoxia is induced by trans-arterial embolization. In some embodiments, one or more hypoxia-inducing agents such as vascular disrupting agents (VDAs) and/or anti-angiogenic agents (AAAs) are administered locally or systemically to create a localized hypoxic region within which a previously-administered or co-administered HABA is activated.

In some embodiments, the vascular disrupting agent (VDA) is DMXAA, a stilbene, or a stilbene derivative. Examples of stilbene derivatives include but are not limited to combretastatin, combretastatin derivatives, cis-3,4',5-trimethoxy-3'-aminostilbene (stilbene 5c), cis-3,4',5-trimethoxy-3'-hydroxystilbene (stilbene 6c), and a prodrug morpholino-carbamate derivative of stilbene 5c. Additional VDAs include but are not limited to: (5S)-5-(acetylamino)-9,10,11-trimethoxy-6,7-dihydro-5H-dibenzo[a,c]cyclohepten-3-yl dihydrogenphosphate (ZD6126), (N-[2-[4-hydroxyphenyl)amino]-3-pyridinyl]-4-methoxybenzenesulfonamide) (E7010 or ABT-751). These compounds induce profound hypoxia selectively in tumors even if administered systemically. The administration of VDAs may be considered a type of chemical embolization, which is to use a chemical agent to achieve the same goal of embolization selectively in a tumor containing region in contrast to the direct occlusion of a vessel in standard embolization. Combinations of VDAs and hypoxia-activated bioreductive agents such as tirapazamine are surprisingly more effective than would be predicted based on the activity of either agent alone in the treatment of solid tumor malignancies. Their activity is synergistic. For example, VDAs given after tirapazamine allow activation of tirapazamine and increase subsequent tumor cell killing by at least 10 fold or higher, compared to the level of tumor cell killing by either agent alone. This strategy may also be combined with embolization described below to be even more effective in inducing tumor hypoxia and tirapazamine activation.

In some embodiments, the hypoxia-inducing agent is an anti-angiogenic agent (AAA). Non-limiting examples of AAA's include bevacizumab, itraconazole, carboxyamidotriazole, TNP-470, CM101, IFNα, IL-12, platelet factor-4, suramin, SU5416, thrombospondin, a VEGFR antagonist, angiostatin, endostatin, 2-methoxyestradiol, tecogalan, tetrathiomolybdate, thalidomide, thrombospondin, prolactin, an $\alpha_v\beta_3$ inhibitor, linomide, tasquinimod, ranibizumab, sorafenib, sunitinib, pazopanib and everolimus. Additional AAAs include but are not limited to: aflibercept, IMC-1C11, vatalanib (PTK-87), N-(2,3-dihydro-3,3-dimethyl-1H-indol-6-yl)-2-[(4-pyridinylmethyl)amino]-3-pyridinecarboxamide (AMG 706), 3-(4-Bromo-2,6-difluoro-benzyloxy)-5-[3-(4-pyrrolidin-1-yl-butyl)-ureido]-isothiazole-4-carboxylic acid amide (CP-547,632), N-(4-(3-amino-1H-indazol-4-yl)phenyl)-N'-(2-fluoro-5-methylphenyl)urea (ABT-869), and cediranib (AXD-2171). Monoclonal antibodies such as bevacizumab have a half-life of over 7 days and work by neutralization of the angiogenic factor VEGF. The deprivation of VEGF eventually prevents new vessel formation in tumors and results in tumor hypoxia due to the consumption of oxygen within the tumor. Small molecular compounds such as sorafenib and sunitinib have half-lives of less than 24 hours and work by directly inhibiting the kinase activity of VEGF receptors.

In some embodiments, combinations of VDAs and AAAs are used to induce tumor hypoxia. In some embodiments, VDAs induce immediate suppression of tumor blood flow to induce hypoxia and activation of HABAs. In some embodiments with induction of tumor hypoxia, AAAs will be used to inhibit compensatory hypoxic responses by the tumor, such as production of VEGF or other angiogenic factors which mobilize endothelial progenitor cells from bone marrow to repair the damaged tumor vasculature. Combination of VDAs with AAAs such as bevacizumab helps to prevent the compensatory effect of VEGF and inhibit the repair process in tumor vessels to enhance the effect of VDAs in causing the tumor to remain in the hypoxic state.

In some embodiments, various combinations of these methods are also contemplated (e.g. embolization plus one or more hypoxia-inducing agents), the overall effect being targeted, localized provision of an activated bioreductive agent, and efficacious killing of tumor cells within or at the targeted site without the side effects usually caused by systemic exposure to bioreductive agents. This enhancement may also permit the use of lower doses of the agents while maintaining an adequate and efficacious level of tumor cell killing, thereby further decreasing toxicity. In some embodiments, components of the combination tumor therapies described herein include one or more anti-angiogenic agents (AAAs), and one or more vascular disrupting agents (VDAs), and a hypoxia-activated bio-reductive agent (HABA). The combination of AAAs and VDAs induce prolonged hypoxia in tumor cells when administered together, and display some efficacy in killing tumor cells on their own. However, their activity is significantly enhanced in a synergistic manner when they are administered as described herein in combination with hypoxia-activated bioreductive agents (HABAs). In some embodiments, the methods described herein are methods of enhancing the anticancer activity of AAAs and/or VDAs by co-administering a HABA. In some embodiments, the methods described herein are methods of enhancing the anticancer activity of HABAs by co-administering AAAs and/or VDAs. In some embodiments, efficacy is further enhanced by the administration of an immune checkpoint inhibitor.

In one example of an embolization procedure, embolization comprises localized therapy used in a tumor or a region containing tumor that is supplied by an identifiable arterial branch, for example, a hepatic artery that supplies a hepatocellular carcinoma, by injecting materials (e.g. Lipiodol, gelfoam, blood clot, particular beads etc.) to induce occlusion of the branch of the artery supplying the region containing the tumor so that the tumor cells cannot obtain adequate blood flow and die. The anatomy of the blood supply of the region and the surrounding normal organs or tissues determines whether the surrounding organs/tissues may experience significant damage due to lack of blood supply after embolization. For example, normal liver is supplied by dual vessels, the hepatic artery and the portal vein, and thus allows the occlusion of the hepatic artery or a branch of it without the consequence of significant damage to normal liver. This procedure is generally performed by interventional radiologists, who place a catheter from the femoral artery in the groin and advance the tip of the catheter to the branch of the hepatic artery that supplies the tumor under fluoroscope X-ray guidance. Once the arterial branch supplying tumor is identified by injection of contrast material, embolizing agents such as Lipiodol or gelfoam, are injected to occlude the branch.

In addition to Lipiodol, other embolizing agents include but are not limited to gelfoam, blood clots, nanoparticles or any clinically proven mechanical agent that can achieve the purpose of vascular occlusion. The administration of embolizing agents and a hypoxia-activated bioreductive agent (HABA) can be carried out in any suitable manner. For example, the HABA may be administered prior to administration of the embolizing agent (e.g. from about 1-120 minutes before), and subsequent administration of the embolizing agent "traps" the HABA in the region. Alternatively, the two agents may be administered together (e.g. using a preparation that includes the two agents in a mixture). In some embodiments, the dosage of HABA that is administered will be in the range of from about 1 mg to about 200 mg (e.g. of tirapazamine), and preferably from about 5 to about 80 mg, for a patient being treated by this method; and the dose of embolizing agent that will be administered will be in the range of from about 5-40 ml, and preferably from about 20-30 ml of e.g. Lipiodol. Sufficient embolizing agent is administered to achieve complete occlusion of the intended branch of the vessel under fluoroscope X-ray examination, to ensure the creation of a hypoxic region or condition in the embolized area. Administration of the embolizing agent is usually carried out by intra-arterial injection. Alternatively, embolization may be carried out by other means such as particular beads to induce occlusion.

In some embodiments, the combination of a HABA and induction of hypoxia induces necrosis of the solid tumor. In some embodiments, the combination induces necrosis of at least 50%, 75%, 80%, 85%, 95%, or more of one or more tumors. Induction of a degree of necrosis may be the degree reached after a specified time following treatment. For example, at least 50% tumor necrosis may be achieved within 1, 2, 3, 4, or more weeks after treatment, or within 1, 2, 3, 4, 5, or more months after treatment. In some embodiments, the degree of tumor necrosis induced by treatment is the maximum level of necrosis observed following treatment, relative to a starting tumor size.

In some embodiments, necrosis of the tumor induces an immune response in the subject against one or more antigens expressed by the tumor. For example, tumor antigens include but are not limited to alphafetoprotein (AFP), carcinoembryonic antigen (CEA), CA-125, MUC-1, epithelial tumor antigen (ETA), tyrosinase, melanoma-associated antigen (MAGE), BCR-abl, p53, immature laminin receptor, TAG-72, HPV E6, HPV E7, BING-4, calcium-activated chloride channel 2, Cyclin-B1, 9D7, Ep-CAM, EphA3, Her2/neu, Telomerase, Mesothelin, SAP-1, Survivin, BAGE, CAGE, GAGE, SAGE, XAGE, NY-ESO-1/LAGE, PRAME, SSX-2, Melan-A/MART-1, Gp100/pmel17, TRP-1, TRP-2, P. polypeptide, MC1R, prostate specific antigen (PSA), b-catenin, BRCA1, BRCA2, CDK4, CML66, Fibronectin, MART-2 or TGRbRII.

Administration of a HABA, inducing hypoxia, and administering an immune checkpoint inhibitor may be sequential or concurrent. In some embodiments, an immune checkpoint inhibitor may be administered sequentially with a HABA and/or inducing hypoxia. For instance, an immune checkpoint inhibitor may be administered alone, prior to either administering a HABA or inducing hypoxia or both. In some embodiments, a checkpoint inhibitor may be administered, followed by a HABA, and later by inducing hypoxia. An immune checkpoint inhibitor may be administered alone after administering a HABA and/or inducing hypoxia. Alternately, an immune checkpoint inhibitor may be administered in combination with a HABA and/or inducing hypoxia.

In some embodiments, an immune checkpoint inhibitor is administered prior to, simultaneously with, or subsequent to inducing hypoxia. When administered prior to inducing hypoxia, the immune checkpoint inhibitor may be administered about 5 minutes to about 24 hours or more before inducing hypoxia. In some embodiments, the immune checkpoint inhibitor is administered about 5, 10, 15, 20, 25, 30, 45 or 60 minutes before inducing hypoxia. In some embodiments, the immune checkpoint inhibitor is administered about 1, 2, 3, 4, 5, 6, 7, 8, 12, 18, 24 hours before inducing hypoxia. In some embodiments, the immune checkpoint inhibitor is administered 1, 2, 3, 4, 5, 6, 7, 8, 9, 10, 11, 12, 13, 14, 21, 28 or more days before inducing hypoxia. In some embodiments, the immune checkpoint inhibitor is administered once before inducing hypoxia. In some embodiments, the immune checkpoint inhibitor is administered multiple times before inducing hypoxia (e.g. 2, 3, 4, 5, 10, 15, 25, or more times). When administered simultaneously, the two agents may be administered as a combination composition (e.g. in a single liquid suspension) or as separate compositions administered at about the same time, through the same or different routes of administration. When administered subsequently to inducing hypoxia, the immune checkpoint inhibitor may be administered after about 5 minutes to about 24 hours or longer after inducing hypoxia. In some embodiments, the immune checkpoint inhibitor is administered about 5, 10, 15, 20, 25, 30, 45 or 60 minutes after inducing hypoxia. In some embodiments, the immune checkpoint inhibitor is administered about 1, 2, 3, 4, 5, 6, 7, 8, 12, 18, 24 hours after inducing hypoxia. In some embodiments, the immune checkpoint inhibitor is administered 1, 2, 3, 4, 5, 6, 7, 8, 9, 10, 11, 12, 13, 14, 21, 28 or more days after inducing hypoxia. In some embodiments, the immune checkpoint inhibitor is administered once after inducing hypoxia. In some embodiments, the immune checkpoint inhibitor is administered multiple times after inducing hypoxia (e.g. 2, 3, 4, 5, 10, 15, 25, or more times).

Administration of the immune checkpoint inhibitor may follow a set dosing schedule until a specified endpoint is obtained, such as a target therapeutic outcome. Examples of dosing schedules include administering an immune checkpoint inhibitor one or more times per day (e.g. 1, 2, 3, or more times); one or more times every 1, 2, 3, 4, 5, 6, 7, or more days; one or more times every 1, 2, 3, 4, or more weeks; one or more times every 1, 2, 3, 4, 5, 6, or more months; or combinations of these (e.g. as in a tapered dosing schedule). In some embodiments, the immune checkpoint inhibitor is administered multiple times over several weeks after inducing hypoxia, for example 1, 2, 3, 4 or more times per day over 1, 2, 3, 4, 5, 6, 8, 12, 16, 20, 24 or 52 weeks after inducing hypoxia.

In general, an immune checkpoint inhibitor is an agent that totally or partially reduces, inhibits, interferes with, or modulates one or more immune checkpoint proteins. Immune checkpoint proteins regulate T-cell activation or function. In some embodiments, immune checkpoint inhibitors increase activity or function of T cells, including but not limited to helper T cells and cytotoxic T cells. In some embodiments, helper T cells include but are not limited to Th1 cells, Th2 cells, and Th17 cells. In some embodiments, immune checkpoint inhibitors increase activity of cytotoxic T cells and helper T cells while decreasing activity of regulatory T cells, in order to increase the immune response against an antigen. In some embodiments, immune checkpoint inhibitors increase proliferation of T cells in response to a tumor antigen. In some embodiments, immune checkpoint inhibitors increase secretion of cytokines by T cells in response to a tumor antigen, including but not limited to IL-6, IL-7, IL-8, IL-9, IL-10, IL-12, IL-13, IL-15, IL-16, IL-17, IL-18, IL-21, IL22, CCL1, CCL2, CCL3, CCL4, CCL5, CCL9, CCL17, CCL19, CCL22, CXCL9, CXCL10, CXCL12, CXCL13, CXCL16, G-CSF, GM-CSF, IFNb, IFNg, IL-1a, IL-1b, IL-2, IL-3, IL-4, IL-5, IL-23, IL-27, MIF, TGFb, TNFa, VEGF, or oncostatin M. In some embodiments, immune checkpoint inhibitors increase cytotoxic T cell activity, or killing of tumor cells, by release of cytotoxins including but not limited to perforin, granzymes, and graulysin. Examples of targets of immune checkpoint proteins include, but are not limited to Adenosine A2A Receptor (A2AR), B7-H3 (also known as CD276), B7-H4 (also known as VTCN1), B and T Lymphocyte Attenuator (BTLA, also known as CD272), Cytotoxic T-Lymphocyte-Associated Protein 4 (CTLA-4, also known as CD152), Indoleamine 2,3-dioxygenase (IDO), Killer-cell Immunoglobulin-like Receptor (KIR), Lymphocyte Activation Gene-3 (LAG3), Programmed Death-1 (PD-1), Programmed Death-1 Ligand (PD-L1 and PD-L2)T-cell Immunoglobulin Domain and Mucin Domain 3 (TIM-3), V-Domain Ig Suppressor of T Cell Activation (VISTA), IL-10 or TGF-beta.

FIG. 1 provides an example diagram illustrating interactions among tumor cells, cytotoxic T cells, antigen presenting cells (APC) and regulatory T cells and regulation of immune checkpoints using various antibodies. For example, illustrated in FIG. 1 are antibodies directed to immune checkpoint receptors including CTLA4, PD-1, and PD-L1. Anti-PD-1 and anti-PD-L1 antibodies may enhance cytotoxic T-cell activity by blocking interaction between PD-1 and PD-L1. Administration of anti-PD-L1 or anti-PD-1 to tumor cells may prevent immune evasion and increase immune-mediated anti-tumor activity. Anti-CTLA4 antibody, also depicted, may enhance immune mediated cytotoxicity of active cytotoxic T cells by blocking immunosuppressive effects of CTLA4 engagement, potentially enhancing T cell proliferation. Such antibodies may decrease activity of regulatory T-cells.

Any of a variety of immune checkpoint inhibitors may be advantageously employed. An inhibitor can be a small molecule, an inhibitory polypeptide (e.g. as in a natural or truncated ligand or receptor), an aptamer, or an antibody. In some embodiments, the inhibitor is an antibody, or an antigen binding fragment thereof that binds to an immune checkpoint protein. In some embodiments, the antibody is a full-length antibody comprising two heavy and two light chain sequences. In some embodiments, the antibody is an IgM, IgG, IgE, IgA, or IgD isotype. In some embodiments, the antibody is an IgG subtype, for example of an IgG1, IgG2, IgG3, or IgG4 subtype. In some embodiments, the antibody is a heavy chain, a light chain, or at least one heavy chain and at least one light chain. In some embodiments, the antibody is an antibody fragment, such as a Fab, Fab' or Fab'$_2$, Fv, Fd, single chain Fv (scFv), disulfide linked Fvs (ddFv), $V_L$, $V_H$, Camel Ig, V-NAR, VHH, trispecific (Fab$_3$), bispecific (Fab$_2$), diabody (($V_L$-$V_H$)$_2$ or ($V_H$-$V_L$)$_2$), tribody (trivalent), tetrabody (tetravalent), minibody ((scFv-CH$_3$)$_2$), bispecific single chain Fv (Bis-scFv), IgGdeltaC$_H$2, scFv-Fc or (scFv)$_2$-Fc, fragment, or single chain antibody. In some embodiments, the immune checkpoint inhibitor is selected from nivolumab, pembrolizumab, atezolizumab, MEDI4736, lambrolizumab, MPDL3280A, BMS-936559, BMS-936558/1VDX-1106, CT-011, pidilizumab, galiximab, AMP-514, MEDI4736, MK-3475, MPDL3280A, IMP321, BMS-986016, IPH2101, MSB0010718C, AUNP 12, tremelimumab, and ipilimumab.

In some embodiments, the immune checkpoint inhibitor is a monoclonal antibody derived from a human or non-human animal (e.g. a mouse or rat), wherein the monoclonal antibody is capable of specifically binding to an immune checkpoint protein. A variety of methodologies for preparing monoclonal antibodies are available. In general, a monoclonal antibody is obtained from or derived from a single clone, including any eukaryotic, prokaryotic, or phage clone. In some embodiments, antibodies comprising one or more heavy and/or light chains from a non-human antibody in addition to portions not derived from a source non-human antibody (such as in a chimeric or humanized antibody) (a) are capable of competing for binding with; (b) retain the functional characteristics; (c) bind to the same epitope; and/or (d) have a similar binding affinity as the corresponding parental non-human antibody.

In some aspects, there are provided monoclonal antibodies comprising one or more heavy and/or light chains from a human antibody. Human antibodies include antibodies having a fully human amino acid sequence, e.g., human heavy and human light chain variable and human constant regions. An antibody that is a non-human antibody may be made fully human by substituting the non-human amino acid residues with amino acid residues that exist in a human antibody. Human antibodies, therefore, include antibodies in which one or more human or non-human amino acid residues have been substituted with one or more amino acids present in any other human antibody.

In some embodiments, an antibody obtained from a non-human animal may be humanized. In some embodiments, a humanized antibody has non-human amino acid residues, for example mouse, rat, goat, rabbit, in one or more complementarity determining regions (CDRs) that specifically bind to the desired antigen in an acceptor immunoglobulin molecule and one or more human amino acid residues in the Fv framework region (FR), which are amino acid residues that flank the CDRs. In some embodiments, a humanized antibody is created by inserting the appropriate CDR segments from the non-human antibody into a human antibody scaffold, wherein the humanized antibody is capable of specifically binding to an immune checkpoint inhibitor. In some embodiments, a humanized monoclonal antibody comprises one or more heavy and/or light chain CDR domains from a first non-human antibody which are used to replace one or more heavy and/or light chain CDR domains from a second human antibody. In some embodiments, the first antibody is obtained from a non-human animal and is capable of specifically binding to an immune checkpoint protein. The CDR domains from the first antibody replace the CDR domains in the second human antibody, wherein the second human antibody is lacking binding specificity for an immune checkpoint protein. This process generates a humanized monoclonal antibody that is capable of specifically binding to an immune checkpoint protein due to the addition of the CDR domains from the first antibody and is not recognized as foreign by the immune system because the remaining antibody domains are derived from a human antibody. In some embodiments, humanized antibodies comprising one or more heavy and/or light chain CDR domains from the first antibody (a) are capable of competing for binding with; (b) retain the functional characteristics; (c) bind to the same epitope; and/or (d) have a similar binding affinity as the corresponding first antibody.

Hypoxia-activated bioreductive agents, hypoxia-inducing agents, and immune checkpoint inhibitors may be formulated as pharmaceutical compositions for administration to a subject, by any suitable administration route. Examples of administration routes include but are not limited to parenteral (including subcutaneous, intravenous, intra-arterial, intraosseous, intracerebral, intracerebroventricular, intrathecal, intramedullary, intraarticular, intramuscular, or intraperitoneal injection), rectal, topical, transdermal, or oral (for example, in capsules, suspensions, or tablets). Pharmaceutical compositions will generally include one or more active agents and one or more pharmaceutically acceptable excipients including but not limited to solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary compounds (e.g., preservatives, antioxidants, antimicrobial agents including biocides and biostats such as antibacterial, antiviral and antifungal agents) can also be incorporated into the compositions. Pharmaceutical compositions may therefore include preservatives, antioxidants and antimicrobial agents. Preservatives can be used to inhibit microbial growth or increase stability of ingredients thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins. An antimicrobial agent or compound directly or indirectly inhibits, reduces, delays, halts, eliminates, arrests, suppresses or prevents contamination by or growth, infectivity, replication, proliferation, reproduction, of a pathogenic or non-pathogenic microbial organism. Classes of antimicrobials include antibacterial, antiviral, antifungal and antiparasitics. Antimicrobials include agents and compounds that kill or destroy (-cidal) or inhibit (-static) contamination by or growth, infectivity, replication, proliferation, reproduction of the microbial organism.

In some embodiments, one or more of the treatment steps may be repeated. For example, the steps of administering a HABA, inducing hypoxia, and administering an immune checkpoint inhibitor may be repeated together one or more times over a course over the course of treatment. In some embodiments, one step is repeated in the absence of the others. For example, after administering the HABA and inducing hypoxia, the immune checkpoint inhibitor may be administered two or more times in accordance with a dosing schedule over a course of treatment. In some embodiments, the immune checkpoint inhibitor is administered 3, 4, 5, 6, 7, 8, 9, 10, 11, 12, 13, 14, 15, 20 or more times after administering the HABA and inducing hypoxia in accordance with a dosing schedule over a course of treatment. In some embodiments, the immune checkpoint inhibitor is administered 3, 4, 5, 6, 7, 8, 9, 10, 11, 12, 13, 14, 15, 20 or more times before administering the HABA and inducing hypoxia in accordance with a dosing schedule over a course of treatment. In some embodiments, the immune checkpoint inhibitor is administered hourly, daily, weekly or monthly after administering the HABA and inducing hypoxia in accordance with a dosing schedule over a course of treatment.

In some embodiments, methods, compositions, and kits of the present disclosure are useful in the treatment of a proliferative disorder of a subject, particular those comprising one or more solid tumors. Examples of proliferative disorders include, but are not limited to Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Metastatic Colorectal Cancer, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof. In some embodiments, a solid tumor is treated. Examples of solid tumors include, but are not limited to, lung cancer, breast cancer, colorectal cancer, bladder cancer, head and neck cancer, ovarian cancer, and pancreatic cancer. In some embodiments, the combination of administering the HABA, inducing hypoxia, and administering the immune checkpoint inhibitor exhibit a synergistic effect in treating a proliferative disorder in the subject.

Efficacy in treating cancer in particular may be measured by any suitable metric. In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, and/or a reduction in the size of at least one tumor such that a human is treated for the proliferative disorder. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. In some embodiments, the primary efficacy parameter used to evaluate the treatment of cancer preferably is a reduction in the size of a tumor. Tumor size can be determined using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

Desirably, the growth of a tumor is stabilized (i.e., one or more tumors do not increase more than 1%, 5%, 10%, 15%, or 20% in size, and/or do not metastasize) as a result of treatment. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the size of a tumor is reduced at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

When a tumor is subject to surgical resection following completion of the therapeutic period, the efficacy of the inventive method in reducing tumor size can be determined by measuring the percentage of resected tissue that is necrotic (i.e., dead). In some embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is about 100%, that is, no tumor tissue is present or detectable.

A number of secondary parameters can be employed to determine the efficacy of the inventive method. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA) prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also efficiently distinguishes small tumors from surrounding tissue (see, for example, U.S. Pat. No. 4,932,412).

In some embodiments, the treatment of cancer in a human patient is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The Karnofsky Performance Scale allows patients to be classified according to their functional impairment. The Karnofsky Performance Scale is scored from 0-100. In general, a lower Karnofsky score is predictive of a poor prognosis for survival. Thus, the treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. The NCI toxicity scale (published April 1999) and Common Toxicity Criteria Manual (updated August 1999) is available through the NCI, e.g., through the NCI interment website at www.ctep.info.nih.gov or in the Investigator's Handbook for participants in clinical trials of investigational agents sponsored by the Division of Cancer Treatment and Diagnosis, NCI (updated March 1998). Desirably, methods described herein are associated with minimal adverse events, e.g. Grade 0, Grade 1, or Grade 2 adverse events, as graded by the CTEP/NCI. However, reduction of tumor size, although preferred, is not required in that the actual size of tumor may not shrink despite the eradication (such as in necrosis) of tumor cells. Eradication of cancerous cells is sufficient to realize a therapeutic effect. Likewise, any reduction in tumor size is sufficient to realize a therapeutic effect.

Detection, monitoring, and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In some embodiments, administering a HABA, inducing hypoxia, and administering an immune checkpoint inhibitor, provides improved therapeutic efficacy over treatment with either agent alone, treatment with both agents delivered simultaneously, and/or treatment with both agents in reverse order. Improved efficacy may be measured using any suitable method, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000%, 10000% or more, using an appropriate measure (e.g. tumor size reduction, duration of tumor size stability, duration of time free from metastatic events, duration of disease-free survival). Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or more, using an appropriate measure (e.g. tumor size reduction, duration of tumor size stability, duration of time free from metastatic events, duration of disease-free survival).

In one aspect, the present disclosure provides kits for enhancing an immune response to a solid tumor in a subject, such as according to any use described herein. Kits can include one or more compositions described herein, in any combination. In some embodiments, the kit comprises (a) a hypoxia-activated bioreductive agent (HABA); (b) a hypoxia-inducing agent or an embolizing agent; and (c) an immune checkpoint inhibitor. Non-limiting examples of HABAs, hypoxia inducing agents, embolizing agents, and immune checkpoint inhibitors are provided above, such as with respect to various methods of the present disclosure. In some embodiments, the kit further comprises instructions for use by a clinician, healthcare provider, or patient, for example printed materials or packaging. Pharmaceutical compositions and other materials in a kit may be contained in any suitable container, and may be in an immediately usable form or require combination with other reagents in the kit or reagents supplied by a user (e.g. dilution of a concentrated composition or reconstitution of a lyophilized composition).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Combination of Tirapazamine and Hepatic Artery Ligation in a Hepatocellular Carcinoma Model Materials and methods: All the HBx transgenic mice were bred and followed-up in a specific pathogen-free facility; the tails of individual mice were subsequently collected for the genotyping process on weaning at 3 weeks of age. Hepatocellular carcinoma (HCC) developed spontaneously in >95% of the male HBx transgenic mice at the age of 17-18 months. Transgenic mice having tumors 0.5-2 cm in diameter were used for the study.

Treatment of tumor-bearing HBx mice with tirapazamine and hepatic artery ligation: The HBx transgenic mice were subjected to the left hepatic artery ligation for 40 min and the silk ligation was subsequently untied. During the studies on the drug effects, 0.9% saline, doxorubicin (10 mg/kg), or TPZ (3 mg/kg) were injected into the tail vein of each mouse for 7 min before the hepatic artery ligation. After completion of the injection, a midline laparotomy was performed to expose the left lobe of liver and liver hilum to dissect the left or common hepatic artery for transient ligation. All mice were anaesthetized with intraperitoneal injection of 400 mg/kg avertin (Sigma-Aldrich, St. Louis, Mo., USA) during experiments. Serial serum samples were collected for evaluating the ALT and total bilirubin by using ARKRAY Spotchem EZ Chemistry Analyzer SP-4430 (Arkray, Inc., Kyoto, Japan) within the first week. After 1 or 7 days, the liver tissues were collected for HE staining.

Histology and morphometric analysis of tumor necrosis: For each mouse, the liver tissue containing the whole tumor and the adjacent non-tumorous region were fixed overnight in 10% formaldehyde and embedded in paraffin. The liver tissue sections (3 µm thickness) crossing the whole tumor were subjected to hematoxylin and eosin (H&E) staining for histological analysis. The percentage of necrosis in each tumor was quantified by dividing the necrotic area by the total tumor area in five cross sections covering the whole tumor, by using the ImageJ software (Version 1.46r, National Institutes of Health, Bethesda, Md., USA). Detailed results are discussed further below.

Example 2: Combination of Tirapazamine and Combretastatin A4 and DMXAA in a Lung Cancer Model Materials and methods: Human lung cancer NCI-H460 cells were purchased from ATCC and used in this study. Cells were sub-cultured within 5 passages before inoculated into the mice. After the animals' acclimation period, approximately $1.5 \times 10^6$ NCI-H460 cells in 200 µL of serum-free media/matrigel (50:50 v/v) were injected subcutaneously to each mouse under anesthesia with 3-4% isoflurane. BALB/c nude mice, male, about 4-5 weeks and 18-20 g in weight were purchased from Shanghai SLAC Laboratory Animal Co. Ltd., China and housed in vivarium in 3-5 mice/cage by treatment group. Mice had free access to food (irradiated, Shanghai SLAC Laboratory Animal Co. Ltd. China) and water (municipal tap water filtered by Mol Ultrapure Water System).

Mice from each group were euthanized with $CO_2$ asphyxiation followed by cervical dislocation at day 18 after the first dose, tumors were collected, weighed, and their pictures taken. The formalin fixed tumors were used for histopathology work. After formalin fixation, the tumors were paraffin embedded to get FFPE blocks. One block was made for each tumor chunk from one mouse. The FFPE blocks were sectioned at about 4 µm thick and processed for H&E staining, histopathology examination, and quantification of tumor necrosis. Detailed results are discussed further below.

Example 3: Induction of Tumor Necrosis and Converting the Tumor into a Cancer Vaccine In Vivo In order to solve the problem of tumor heterogeneity and genomic instability, the ideal cancer vaccine is the self-tumor of each patient. However, the tumor itself is typically not very immunogenic, and the degree of anti-tumor immunity is generally not sufficient even in the presence of immune checkpoint inhibitors alone. An immune response may be enhanced by inducing tumor necrosis, which is associated with strong inflammatory responses that lead to a presentation of tumor-associated antigens to T cells and increase the population of tumor-specific T cells. One approach of induction of tumor necrosis is applicable in cancers within liver, for example, which is an organ with dual blood supplies from portal vein and hepatic artery that allow embolization of the tumor-supplying hepatic artery without significant damages to normal liver. The strategy to induce tumor necrosis is a combination of tirapazamine, a hypoxia-activated agent, and transarterial embolization (TAE) to create tumor hypoxia which activates tirapazamine to induce tumor necrosis. The efficacy of the combination was confirmed in HBx transgenic mice model.

The animal model used for the study is transgenic mice expressing HBx, an oncogene of hepatitis B virus which was shown to be capable of inducing liver cells transformation into tumor. The HBx transgenic mice spontaneously develop hepatocellular carcinoma at approximately 18 months. The tumor lesions have no baseline tumor necrosis, and it is ideal to use for investigation of the degree of tumor necrosis induced by the combination of tirapazamine and hepatic artery ligation (HAL). The effective dose of tirapazamine in the HBx transgenic mouse model combined with transient HAL was first established to be 3 mg/kg in a titration study first. Next, the efficacy of tirapazamine in combination with HAL was investigated and compared with a commonly used chemotherapy agent, doxorubicin, in TACE. A small group was first tested to compare the effects of saline (n=1), doxorubicin (10 mg/kg, n=1) and tirapazamine (3 mg/kg, n=1) to treat HBx transgenic mice that had palpable HCC, along with transient left HAL. Mice were sacrificed 1 day after treatment with tirapazamine and transient left HAL. The ALT level had a much higher elevation in tirapazamine treated mice than in doxorubicin-treated mice. The histopathological examination at Day 1 post-treatment showed that tirapazamine induced more than 99% necrosis in the HCC within the territory of HAL, in contrast, only about 5% necrosis in doxorubicin-treated HCC. This result indicated that tirapazamine was much more effective than doxorubicin when combined with HAL to induce tumor necrosis.

The same study was conducted to examine the histopathology changes at 7 days post treatment. The number of mice used for each group were saline (n=2), doxorubicin (10 mg/kg, n=2) and tirapazamine (3 mg/kg, n=3). Tumor blood flow was monitored by the oxyFlo sensor and showed blood flow dropped to 30% by HAL for HCC treated with either tirapazamine or doxorubicin, which was sufficient to induce tumor hypoxia.

Figure 2:
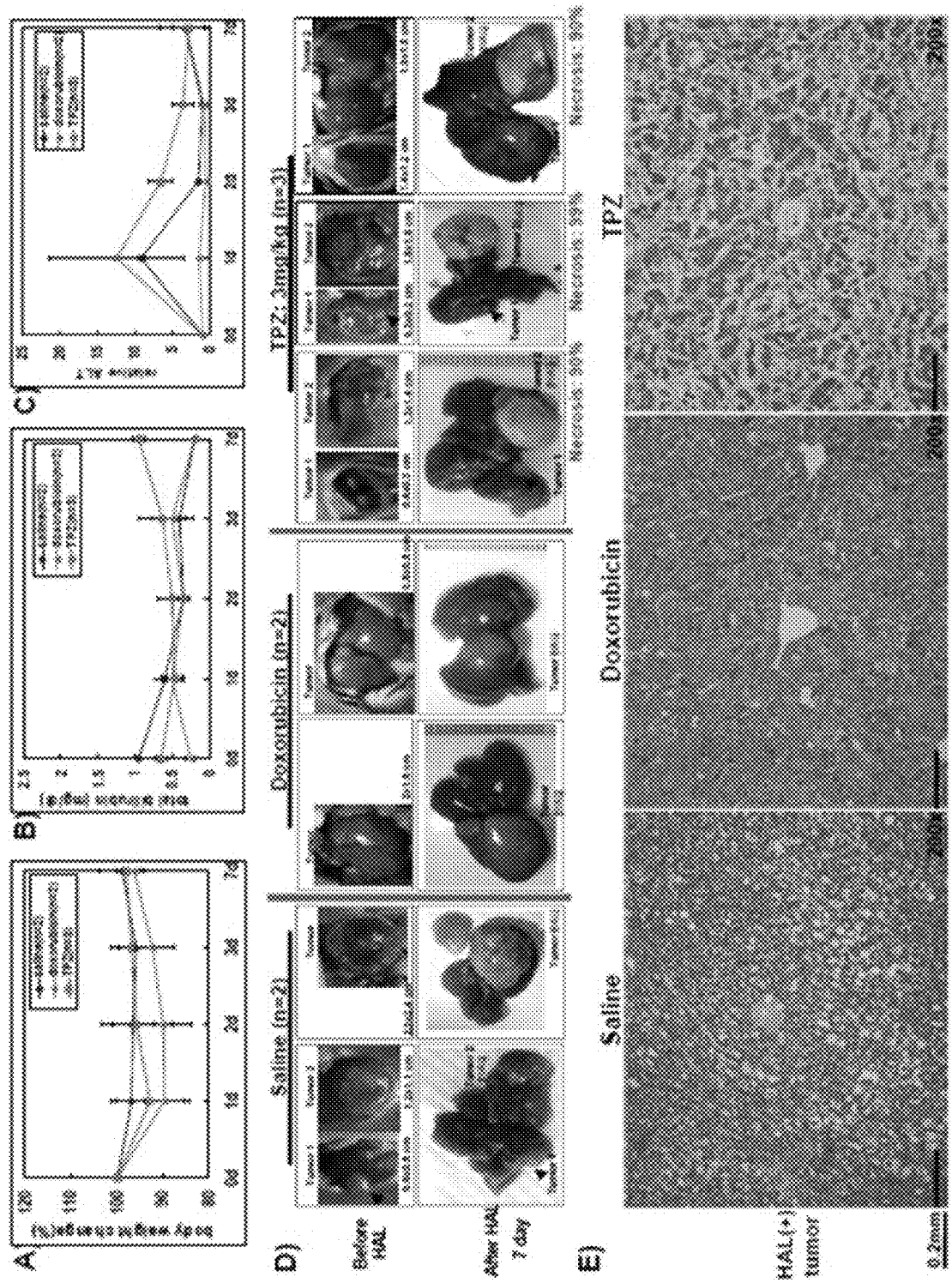
FIG. 2 illustrates example results for comparison of the combinations of left hepatic artery ligation (HAL) with saline, doxorubicin, or tirapazamine in the HBx transgenic mouse model. Tumor-bearing HBx transgenic mice were treated with normal saline, tirapazamine (3 mg/kg IV injection from tail vein) or doxorubicin (10 mg/kg) followed by left hepatic artery ligation for 40 min. Mouse weight, bilirubin, and ALT were measured at various days after treatment. Mice were sacrificed at day 7 for histological analysis of the hepatocellular carcinoma (HCC) tumor.

Analysis of mouse body weight showed no statistically significant change, but the average weight in doxorubicin-treated mice appeared slightly lower (FIG. 2A). The levels of total bilirubin in serum were all within the normal range among the three groups throughout the 7 days (FIG. 2B). The serum ALT level reached a peak on Day 1 in the group treated with tirapazamine and transient left HAL (FIG. 2C). Subsequently, ALT levels decreased and returned to normal around Day 3. Doxorubicin and transient HAL also induced ALT elevation on Day 1 but less than tirapazamine and left HAL, and ALT in both groups recovered to normal levels by Day 2. During dissection on Day 7, it was evident that tumor necrosis occurred in HCC treated with tirapazamine and transient HAL by its pale color, but not in HCC from mice treated with saline or doxorubicin (FIG. 2D). Histopathologic analysis by H&E staining confirmed that HCCs in the territory of the left HAL had 90-99% necrosis after the combination treatment of Tirapazamine and left HAL. Little to no pathological changes were detected in HCCs treated with saline or doxorubicin combined with left HAL (FIG. 2E). Since these mice frequently had multiple HCC, there were tumor nodules present in the right lobe that served as internal controls. Tumor necrosis did not occur in any of the right lobes in any animal. In the tumor-free part of the left lobe of the liver, there was no evidence of necrosis seen, indicating that the combination of tirapazamine and left HAL did not result in any significant injury in the normal liver of the same lobe by Day 7. Although there may have been transient damage on Day 1 as suggested by elevation of ALT, it was fully recovered on Day 7.

The study result indicates that the combination of tirapazamine and TAE is better than TAE alone or the combination of doxorubicin and TAE in inducing tumor necrosis. Doxorubicin is currently used as a chemotherapy component of TACE (trans-arterial chemoembolization) for the treatment of intermediate stage HCC. The data described above indicates that to achieve the maximal tumor necrosis to trigger immunity against HCC, using tirapazamine in combination with TAE is far better than TACE with doxorubicin.

Figure 3:
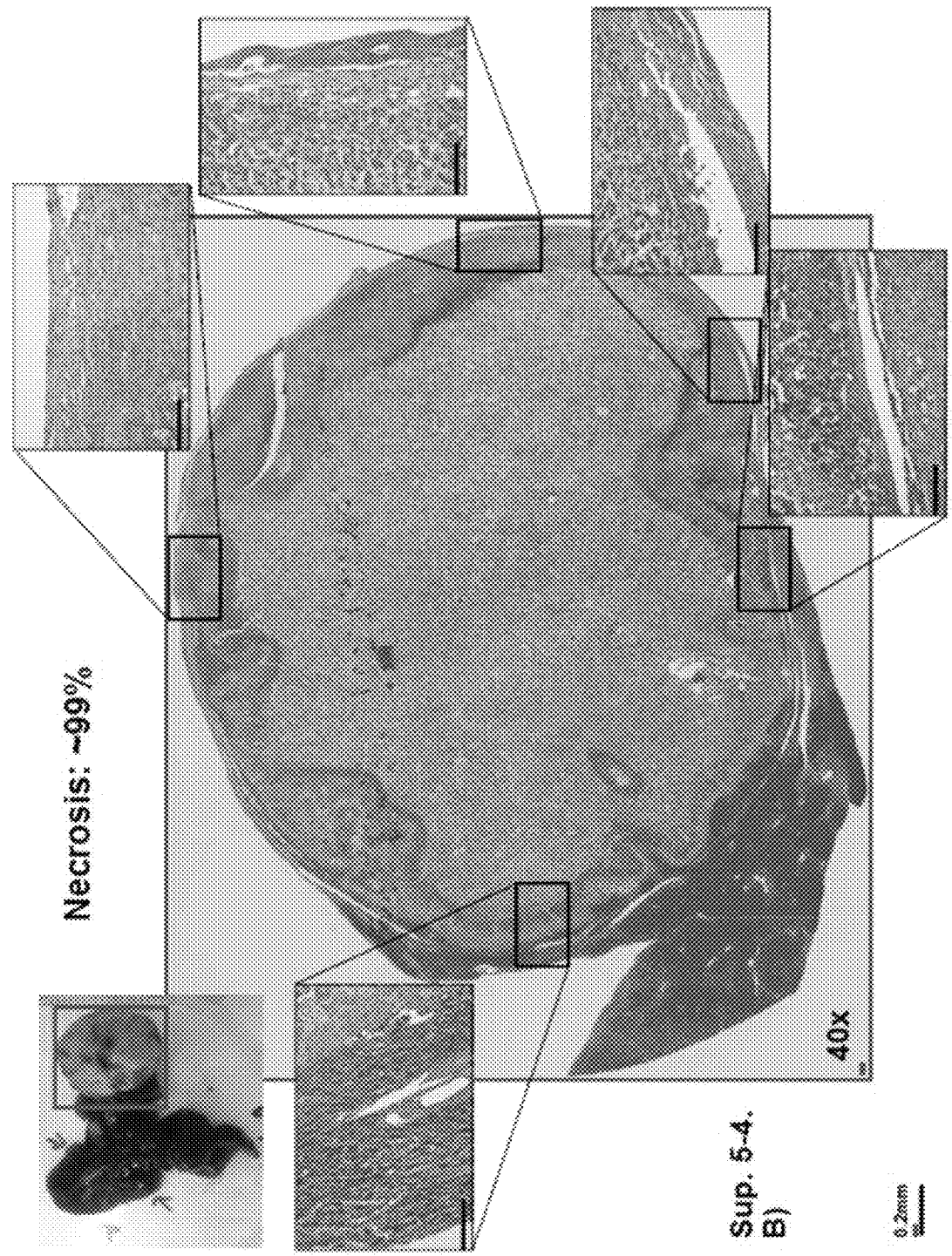
FIG. 3 provides images of tissue illustrating effects of inducing tumor necrosis and triggering an inflammatory reaction after treatment of HCC with tirapazamine and hepatic artery ligation. Tumor-bearing HBx transgenic mice were treated with tirapazamine (3 mg/kg IV injection from tail vein) followed by left hepatic artery ligation for 40 min. Mice were sacrificed at day 7 for histological analysis of the HCC tumor. Shown is the composite picture of the whole tumor that is assembled from multiple histological sections with near complete (99%) tumor necrosis. Also noted is that the margin of necrotic tumor has a high degree of inflammatory cell infiltration (all enlarged magnified inserts).

The same model was then used to examine the degree of tumor necrosis after treatment and whether tumor necrosis induced by this approach is associated with significant inflammatory response, which facilitates phagocytosis of necrotic debris by macrophages/dendritic cells that serve as antigen presenting cells. In the higher power view (FIG. 3), the percentage of tumor necrosis was determined by assembling multiple pieces of histological sections to assess the overall percentage of tumor necrosis after treatment with tirapazamine and HAL. It was observed that over 99% of the entire tumor became necrotic. The peripheral region of the necrotic tumor was examined in details to look for inflammatory cell infiltrate. The inserts of FIG. 3 show that the peripheral region of the necrotic tumor had very strong inflammatory infiltrates, consistent with the theory that necrosis triggers an inflammatory response.

Example 4: Inducing Tumor Necrosis in Patients with Hepatocellular Carcinoma Who are Suitable for Embolization Using a Combination of Tirapazamine and Trans-Arterial Embolization (TAE)

In order to test the clinical tolerability and efficacy of tirapazamine combined with TAE in humans, a phase I dose-defining study was initiated in US major medical centers to examine the tolerability, preliminary efficacy and determine the recommended phase 2 dose (RP2D) of tirapazamine when combined with TAE. HCC patients enrolled were Child-Pugh class A, were not surgical candidates and had up to 4 tumor lesions with no tumor lesion size greater than 10 cm and were suitable for embolization. The results of the first 12 evaluable patients were available for analysis.

In the first two cohorts, tirapazamine was administered by systemic IV infusion at 5 and 10 mg/m$^2$, which are significantly lower than the dose used in prior phase 3 studies at 250-330 mg/m². Doses were selected based on an equivalent of ¹/₁₀ of the toxic dose estimated from the mouse studies of tirapazamine and left hepatic artery ligation and the potent results demonstrated in animal model study (Example 1). Three patients were enrolled in either cohort. Treatment was tolerated by all with no observed toxicities or dose limiting toxicities (DLT). Subsequently, the route of administration was switched to intra-arterial (IA) via the hepatic artery based on well tolerated profile for IA administration followed by hepatic artery ligation in a rat toxicology study. The starting clinical dose of IA route was 5 mg/m², which is 50% of the IV dose shown to be tolerated. The doses of IA cohorts were then up-titrated to 10 mg/m² with 3 patients in either cohort. Treatment was tolerated by all patients with no observed toxicities or dose limiting toxicities (DLT).

Figure 4:
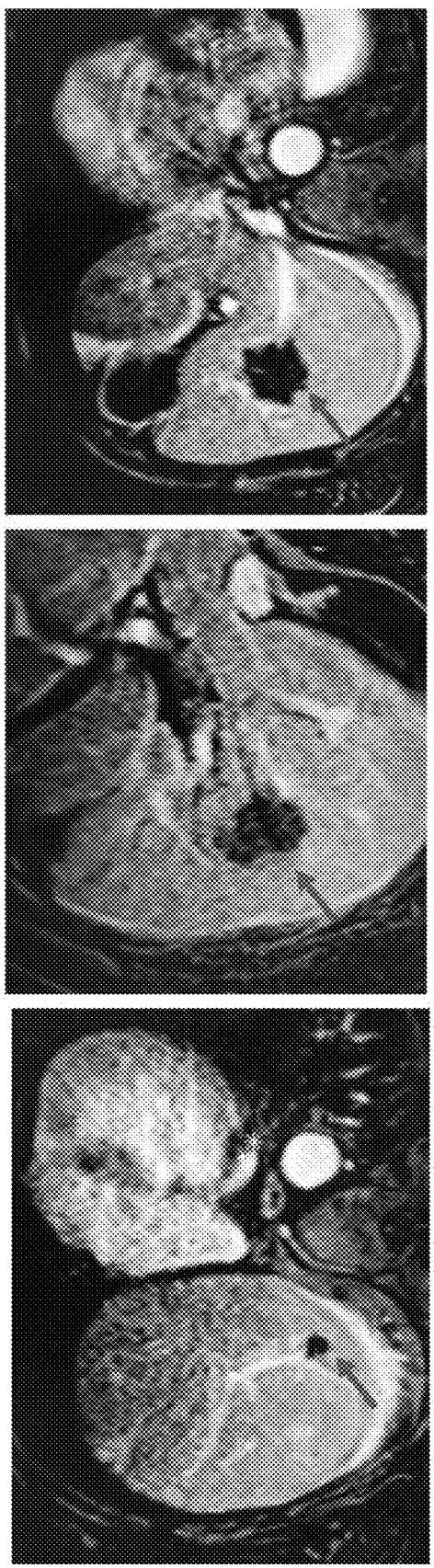
FIG. 4 provides the representative pictures of contrast enhanced MM scans of two patients who achieved complete response (CR). These patients received 5 and 10 mg/m$^2$ tirapazamine, respectively, before trans-arterial embolization. The follow-up MRI scans were done at $6^{th}$ week after the embolization procedure. The dark areas highlighted by arrows are the tumor, which has no evidence of contrast enhancement and is assessed as complete tumor necrosis or CR.

The preliminary efficacy of the first 12 patients was analyzed and is exemplified in FIG. 4. Efficacy outcome is read by contrast MRI based on modified Response Evaluation Criteria In Solid Tumors (RECIST) criteria so that only the size of the viable tumor was measured. The preliminary efficacy analysis shows a robust activity with 6/12 evaluable patients having no contrast enhanced lesion such as in (FIG. 4), indicating that all tumor tissue had become necrotic, i.e. achieving complete response (CR) by modified RECIST after a single treatment of tirapazamine with TAE. Three additional patients had over 30% necrosis or partial response (PR). The overall response rate (CR+PR) was 83%. This result is significantly better compared with a historic control of CR+PR at 50% reported in a meta-analysis of over 10,000 patients who underwent trans-arterial chemoembolization (TACE) in the past.

Example 5. Tumor Shrinkage in Size for Untreated Lesions in Patients Who had Other Tumor Lesions Treated with Tirapazamine and Trans-Arterial Embolization In the 12 patients treated in the phase I clinical study, several patients had multiple tumor lesions and could not be treated at one single procedure. One patient had three lesions at the sizes of 15, 26, 10 mm, respectively, in the largest diameter. Due to the vascular supplies, the interventional radiologist elected to treat the 26 and 10 mm lesions since they were located nearby each other. The third lesion at 15 mm was left untreated at the first procedure. When a follow-up MRI at the 6$^{th}$ week was performed, it was found that the two treated lesions achieved CR; and the third lesion, which was 15 mm in the baseline, shrank to only 9 mm in the largest diameter. One potential explanation consistent with the finding is that the treatment of the two lesions induced anti-tumor immunity, which rendered the untreated lesion smaller. In other words, the two treated lesions potentially served as a cancer vaccine that enhanced that patient's immune system to control the remaining tumor lesions.

Example 6: Inducing Tumor Necrosis Using Tirapazamine and a Vascular Disrupting Agent in Non-Liver Tissue Another approach to induce tumor necrosis is for the application in various solid tumors that less amenable to embolization procedures. The approach to induce hypoxia in solid tumors in this example is through the use of vascular disrupting agents, such as DMXAA (5,6-Dimethylxantheonone-4-acetic acid, also called ASA404 or Vadimezan), or stilbene derivatives including combretastatin A4, combretastatin A4 phosphate, or cis-3,4',5-trimethoxy-3'-aminostilbene (Stilbene 4a). These compounds have been demonstrated to be able to shut down tumor blood flow and induce tumor hypoxia (Chaplin D J, 2006) (Tozer G M, 2005). In this example, the combination of tirapazamine and combretastatin A4 or DMXAA was examined in a lung cancer xenograft model as an example to test their ability to induce tumor necrosis.

A lung cancer mouse model was generated by injection of NCI-H460 human lung cancer cells subcutaneously in BALB/c nude mice to form tumor xenografts to test the combination of tirapazamine and two vascular disrupting agents, combretastatin A4 or DMXAA. When the average tumor volume reached about 480-550 mm³ (around 1 cm in diameter) and tumors were solid and increasing in size, tumor-bearing mice were dosed with tirapazamine (30 mg/kg i.p.), and either combretastatin A4 (10 mg/kg i.v.), or DMXAA (20 mg/kg i.v.) once weekly for two doses to ensure the combination was capable of inducing tumor necrosis. Tirapazamine was given first, then 3-5 min later combretastatin A4 or DMXAA was injected. Both vascular disrupting agents caused nearly immediate shutdown of the tumor vasculature. The animals were observed for any abnormalities for up to three weeks after the first dose.

Figure 5:
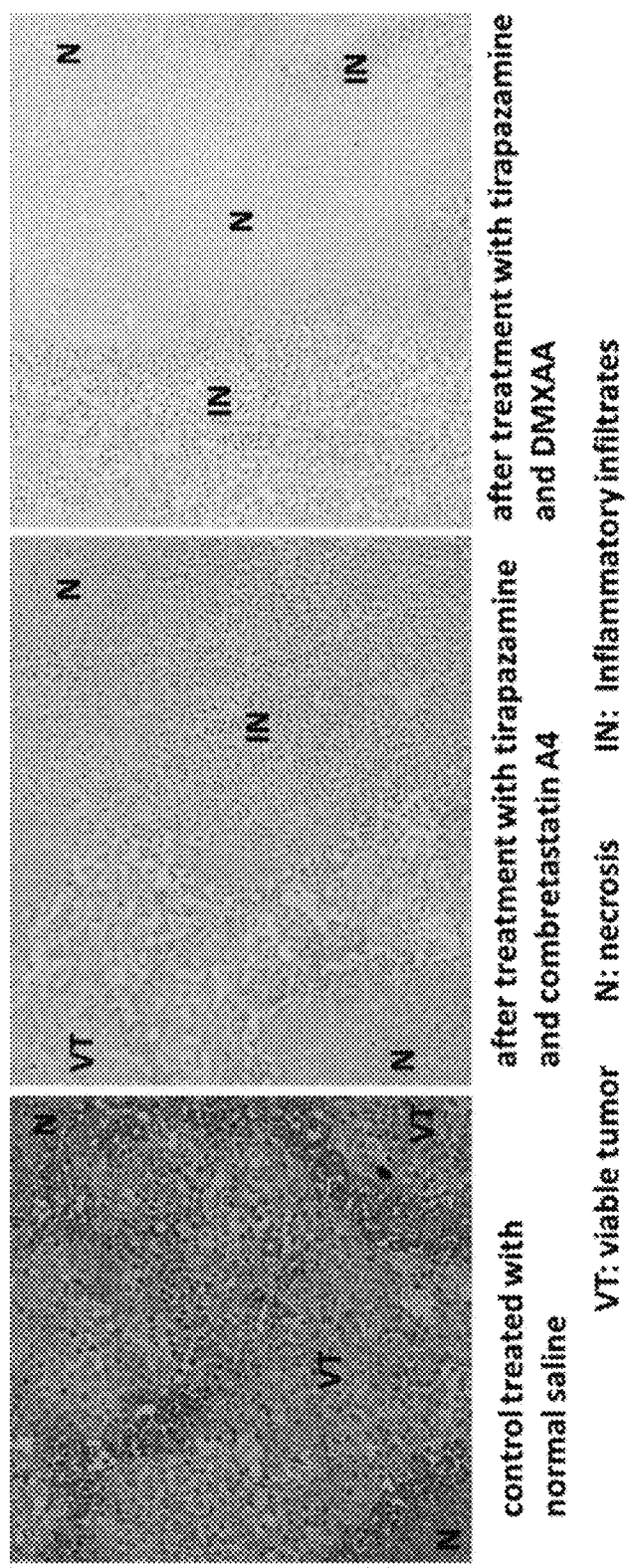
FIG. 5 provides images of tissue illustrating effects of inducing tumor necrosis and triggering of inflammatory response by tirapazamine and vascular disrupting agents. NCI-H460 cells were injected subcutaneously in BALB/c nude mice to form tumor xenografts. Once the tumors grew to 10 mm in diameter in size, mice were treated with tirapazamine (30 mg/kg IP) plus (A) combretastatin A4 (10 mg/kg IV) or (B) DMXAA (20 mg/kg IV) (Chaplin D J, 2006). Mice were sacrificed 3 weeks after the first treatment and tumors were dissected for H&E staining. Shown are representative pictures of histology. The areas of tumor necrosis and the nearby inflammatory infiltrates are indicated.

The treated mice were sacrificed at the end of week 3 and tumors were harvested for histology examination by H&E staining. Most tumors exhibited ~50-70% tumor necrosis, whereas the control tumor treated with normal saline had less than 20% necrosis. Representative histopathological pictures are shown in FIG. 5. The key findings are a large area of tumor necrosis after treatment, and there are strong inflammatory infiltrates surrounding the necrotic tumor. This result is consistent with the previous finding in HCC that tumor necrosis is associated with strong inflammatory reaction and thus capable of boosting the anti-tumor immunity.

Once the self-tumor "vaccination" is accomplished by the necrotic tumor induced by the combination of tirapazamine with either TAE or vascular disrupting agents, the induced T cell population may still be ineffective in ultimately controlling the tumor in the long-term due to immune suppressive effect of the tumor microenvironment. Therefore, a combination using a checkpoint inhibitor as a maintenance therapy to eliminate the immune suppressive effect within the tumor is proposed.

Example 7: Combination of a HABA, a Hypoxia Inducing Agent, and an Immune Checkpoint Inhibitor Administered in a Lung Cancer Model In a study investigating the effects of administering immune checkpoint inhibitor in combination with a hypoxia activated bioreductive agent and a hypoxia-inducing agent, anti-mPD-1, tirapazamine (TPZ), combretastatin A4 phosphate, 5,6-Dimethylxantheonone-4-acetic acid (DMXAA), and various combinations thereof were administered in the treatment of subcutaneous 3LL lung syngenic cancer model in C57BL/6 mice.

The C57BL/6 mice, male, were purchased from Shanghai Laboratory Animal Center (SLAC, (Shanghai, China, SOCK 2012-0002); age: 6-8 weeks; body weight: 18-22 g) The mice were kept in SPF room at constant temperature and humidity with 4 animals in each cage. The temperature was 20.5-24.5° C. The humidity was kept at 40%-75%. The light cycle comprised 12 hours of light and 12 hours of dark. The mice were kept in polycarbonate cages (325 mm×210 mm×180 mm). The cage bedding material was corn cob, changed twice per week. The mice had free access to irradiation sterilized dry granule food during the entire study period and free access to sterile drinking water.

The 3LL tumor cells were maintained in vitro as a monolayer culture in DMEM medium supplemented with 10% heat inactivated fetal bovine serum and L-glutamine (2 mM) at 37° C. in an atmosphere of 5% $CO_2$ in air. The tumor cells were routinely subcultured twice weekly by trypsin-EDTA treatment. 3LL tumor cells growing in exponential growth phase were harvested and counted for inoculation.

C57BL/6 mice were inoculated under the right flank with 3LL tumor cells ($2\times10^5$ cells) in 0.05 mL of phosphate buffered saline (PBS) for tumor development. Treatments were started at 9 days after inoculation when the average tumor volume reached about 455.64 $mm^3$. The treatment administration in each study group are shown in FIG. 6 ("N" denotes animal number; "i.v." denotes intravenous injection, "i.p." denotes intraperitoneal injection). Dosing volume was adjusted based on body weight (0.1 mg/10 g). When the tumor size of 3LL syngeneic model reached approximately 4000 $mm^3$ at 11 days after test articles treatment, the tumor was surgically resected and fixed into 10% formalin for H&E staining and immune markers staining with F4/80.

The total tumor tissues were placed into 10% Neutral Buffered Formalin after trimming as soon as possible. The fixed tissues were processed into block(s) via dehydration, clearing, infiltration. The procedure can be done by automated tissues processor. To prepare formalin-fixed paraffin embedded samples, the following steps were followed. Molten paraffin was poured into embedding molds. The processed tissues were placed into the molds with applicable embedding surface face-down (to avoid generating bubbles). The paraffin molds comprising tissues were put onto a cryo-stage. The paraffin blocks were then sectioned into slices having a thickness of 5 μm using a microtome. The appropriate sections were put into 45° C. distilled water bath. Unfolded sections were pulled out of the water bath via slide, then slides were air-dried.

For hematoxylin and eosin (H&E) staining, the paraffin slides were placed into oven with 60° C. for about 2 hours and then cooled in room temperature. The paraffin slides were then dewaxed, H&E stained, dehydrated, cleared, and mounted. A coverslip was applied using a permanent mounting media. Finally, the slide underwent microscopic examination and photos were taken. Calculation of the percentage of tumor necrosis (%) was determined by dividing the tumor necrosis area by the total tumor slide area.

Figure 7:
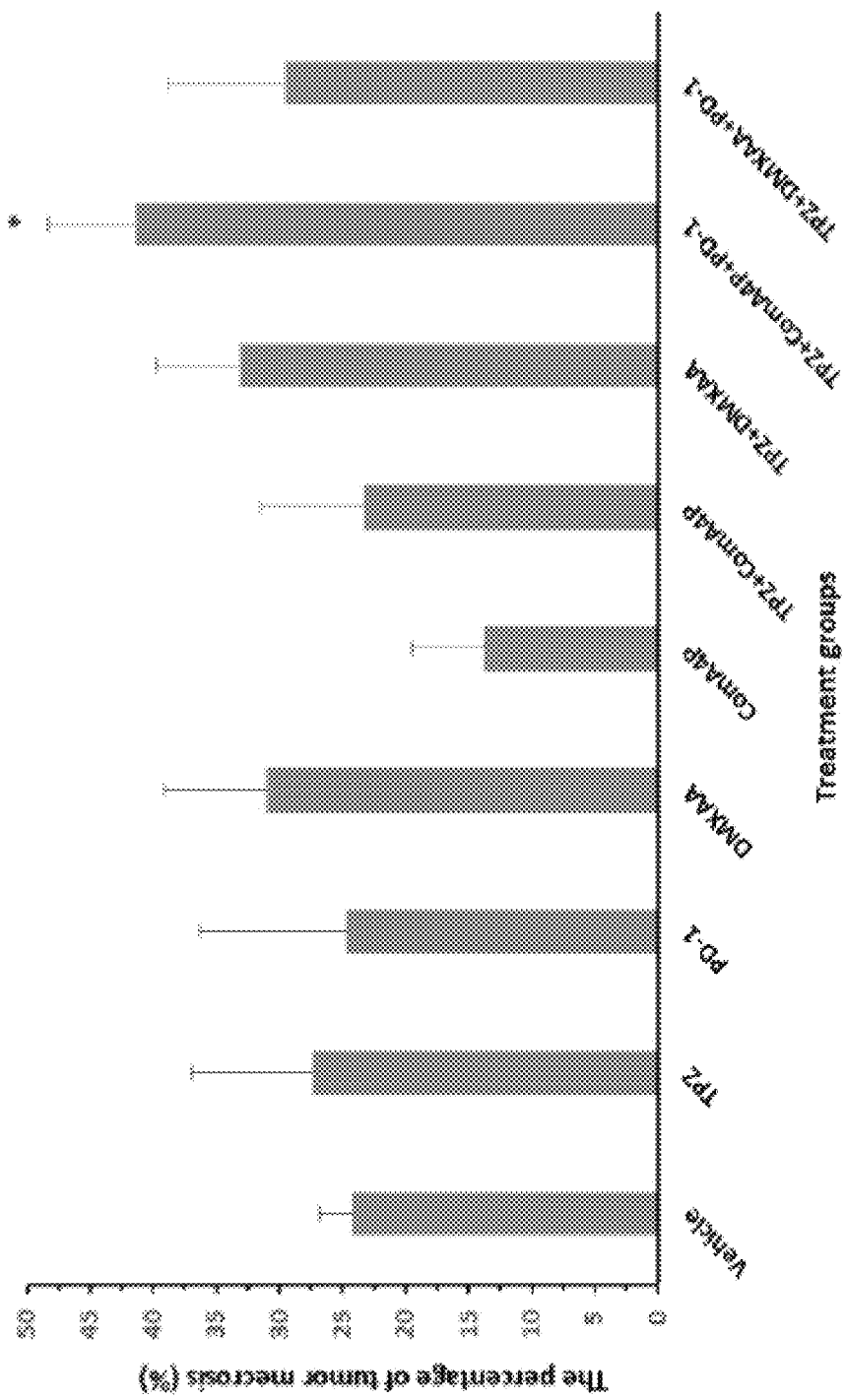
FIG. 7 provides results of percentage of tumor necrosis based on hematoxylin and eosin (H&E) staining of formalin-fixed paraffin embedded tissue following administration of anti-mPD-1, tirapazamine (TPZ), combretastatin A4 phosphate, 5,6-Dimethylxantheonone-4-acetic acid (DMXAA), and various combinations thereof, in the treatment of subcutaneous 3LL lung syngenic cancer model in C57BL/6 mice. The asterisk (*) denotes statistical significance ($P<0.05$) compared to the Vehicle group, as determined by the Mann-Whitney test.

FIG. 7 is shows the tumor necrosis rate after treatment with test articles including anti-mPD-1, tirapazamine (TPZ), combretastatin A4 phosphate, 5,6-Dimethylxantheonone-4-acetic acid (DMXAA), and various combinations thereof, as indicated by H&E staining. The asterisk (*) denotes statistical significance ($P<0.05$) compared to Vehicle group, by Mann-Whitney test. The combination of TPZ, Combretastatin A4 phosphate, and anti-m PD-1 showed a significant increase in tumor necrosis rate compared to the Vehicle group. FIG. 8 provides the data depicted in the FIG. 7.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of enhancing an anti-tumor immune response in a subject in need thereof, the method comprising:
    (a) administering a hypoxia-activated bioreductive agent (HABA) that is tirapazamine to said subject suffering from a cancer that has a liver tumor and a lung tumor, or a cancer that has microsatellite-stable metastatic colorectal cancer (mCRC-MSS) and a lung tumor;
    (b) inducing hypoxia by trans-arterial embolization of one or more blood vessels supplying said liver tumor or said mCRC-MSS, and
    (c) administering to said subject an effective amount of an immune checkpoint inhibitor of programmed cell death protein 1 (PD-1) to enhance an anti-tumor immune response in said subject, wherein said immune checkpoint inhibitor is an anti-PD-1 antibody, wherein the anti-PD-1 antibody is nivolumab or pembrolizumab;
    wherein the combination of (a) administering said HABA and (b) inducing hypoxia induces necrosis of said liver tumor or said mCRC-MSS; and
    wherein the combination of (a) administering the HABA, (b) inducing hypoxia, and (c) administering the anti-PD-1 antibody exhibits a synergistic effect, which wherein said synergistic effect comprises a size reduction of said lung tumor greater than a corresponding size reduction achieved in the absence of the combination of (a) administering said HABA and (b) inducing hypoxia, thereby enhancing said anti-tumor immune response in said subject.

2. The method of claim 1, wherein the combination of (a) administering the hypoxia-activated bioreductive agent and (b) inducing the hypoxia induces necrosis of at least 75% of said liver or colerectal tumor.

3. The method of claim 1, wherein step (b) comprises embolizing the one or more blood vessels by administering an embolizing agent.

4. The method of claim 1, wherein step (b) is performed after step (a).

5. The method of claim 1, wherein step (c) comprises administering the immune checkpoint inhibitor two or more times after step (b).

6. The method of claim 1, wherein administering the immune checkpoint regulator is effective in maintaining said liver or colerectal tumor at a size that is less than 50% of a pre-treatment size for at least 6 months.

7. The method of claim 1, wherein step (c) is performed prior to step (b).

8. The method of claim 1, wherein step (c) is performed simultaneously with step (b).

9. The method of claim 1, wherein step (c) is performed subsequent to step (b).

10. The method of claim 1, wherein said liver tumor is hepatocellular carcinoma (HCC).

* * * * *